United States Patent [19]

Server

[11] Patent Number: 4,626,524

[45] Date of Patent: Dec. 2, 1986

[54] ANTIVIRAL PEPTIDES

[75] Inventor: Alfred Server, Boston, Mass.

[73] Assignee: The General Hospital Corporation, Boston, Mass.

[21] Appl. No.: 645,554

[22] Filed: Aug. 30, 1984

[51] Int. Cl.$^4$ .................. A61K 37/02; C07K 7/10; C07K 7/08; C07K 7/06; C07K 5/10
[52] U.S. Cl. ........................................ 514/13; 514/14; 514/15; 514/16; 514/17; 514/18; 530/325; 530/330; 530/326; 530/327; 530/328; 530/329
[58] Field of Search .................. 260/112.5 R; 514/13, 514/14, 15, 16, 17, 18

[56] References Cited

PUBLICATIONS

Richardson, C. D. et al., Virology, 105: 205–222 (1980).
Miller, F. A. et al., Applied Microbiology, 16: 1489–1496 (1968).
Nicolaides, E. et al., Journal of Medical Chemistry, 11: 74–79 (1968).
Nornby, E., Virology, 44: 599–608 (1971).

*Primary Examiner*—Delbert R. Phillips
*Attorney, Agent, or Firm*—Saidman, Sterne, Kessler & Goldstein

[57] ABSTRACT

The present invention provides peptides of a sequence which is similar or identical to the amino terminal sequence of the $F_1$ chain of mumps virus. A variety of peptides are disclosed ranging from oligopeptides to dodecapeptides.

13 Claims, 5 Drawing Figures

| | 1 | | | | 5 | | | | 10 | | | | 15 | | | | 20 |
|---|---|---|---|---|---|---|---|---|---|---|---|---|---|---|---|---|---|
| Mumps virus | Phe | Ala | Gly | Ile | Ala | Ile | Gly | Ile | Ala | Ala | Leu | Gly | Val | Ala | Thr | Ala | Ala | Gln | Val | Thr |
| SV5 | --- | --- | --- | --- | Val | Val | --- | --- | Leu | --- | --- | --- | --- | --- | --- | --- | --- | --- | --- | --- |
| Sendai Virus | --- | Phe | --- | --- | Ala | Val | --- | --- | Thr | Ile | --- | --- | --- | --- | --- | --- | --- | --- | Ile | --- |
| NDV | --- | Ile | --- | --- | Ala | Ile | --- | --- | Gly | Val | --- | --- | --- | --- | --- | --- | --- | --- | Ile | --- |

ANTIVIRAL PEPTIDES

BACKGROUND OF THE INVENTION

1. Field of the Invention

The present invention relates to synthetic oligo- and polypeptides, compositions containing same, and methods of use, including the treatment of viral infections.

2. Brief Description of the Background Art

Generally speaking, antiviral therapy has proceeded along two separate but interrelated pathways. The first is the development of compounds that act by directly influencing the virus/host cell interaction as a means of aborting the infection. The second is more broadly directed at altering the host's immune functions to prevent viral entry or enhance viral clearance at the level of the host organism. Both approaches have required identification of the specific viral agent in question and detailed understanding of the events of viral replication, in terms of molecular interactions at the cellular level and pathogenic mechanisms at the level of the entire host (see generally Server, A. C. and Wolinsky, J. S., *Human Motor Neuron Diseases*, edited by Lewis P. Rowland (Raven Press, New York, 1982), the chapter entitled "Approaches to Antiviral Therapy," at pp. 519-546.)

Among specific antiviral chemotherapeutic agents are drugs that interfere with virus adsorption to, penetration into, and uncoating in the host cell. Inhibition of these early steps in virus replication, which occur prior to utilization of a significant number of host processes, would be associated with limited host toxicity. Few drugs, however, have been shown to act at these steps in virus infection. Among these are included heparin, amantadine, and a number of oligopeptides.

It has been suggested that a number of carbobenzoxyoligopeptides, which inhibit infection by some members of the herpes, orthomyxovirus, and paramyxovirus families may act by preventing virion penetration. Activity of these agents in culture was independently reported by several groups in 1968. See, for example, Miller, F. A. et al., *Appl. Microbiol.* 16: 1489-1496 (1968); or Nicolaides, E. et al., *J. Med. Chem.* 11: 74-79 (1968). Carbobenzoxy D-phenylalanine-L-phenylalanyl-nitro-L-arginine (SV-4814) is among the most effective of these agents, with the greatest activity shown against measles virus (Miller, F. A. et al., supra). The site of action of this agent in inhibiting measles virus infection has been demonstrated (Norrby, E., *Virology* 44: 559-608 (1971)). SV-4814 has no effect on virus adsorption or virus-induced hemagglutination, yet it markedly prolongs the period during which adsorbed virions are susceptible to neutralization by extracellular antibody. It has been concluded therefore that the drug inhibits virion penetration, which, in the case of measles, is thought to occur by fusion of virion envelope with the host cell membrane. The activity of the drug is generally thought to derive from its sequence homology with the amino-terminus of the viral protein that mediates fusion (fusion, or F, protein). For example, Richardson, et al. (*Virology* 105: 205-222 (1980)), has demonstrated that the inhibition of paramyxovirus activity by SV-4814 and closely related oligopeptides was amino acid sequence-specific. For example, in the case of Sendai virus, the most effective inhibitor was the oligopeptide with the closest sequence homology to the aminoterminus of the viral fusion protein.

Although the ultimate value of these peptides as clinically useful antiviral agents still remains to be determined, preliminary studies indicate that these inhibitors of the prior art have limited toxicity in vitro and can be safely administered orally to laboratory animals. Richardson, et al., supra, have also demonstrated that oligopeptides with activity against measles and other paramyxoviruses and at least one orthomyxovirus (influenza A) can be synthesized, pointing to a great potential for these agents.

Among oligopeptides of relevance to those claimed in the present invention can be mentioned the following: Cbz—D—Phe—L—Phe—Gly (where Cbz is the carbobenzoxy group), Cbz—L—Phe—L—Phe, Cbz—D—Phe—L—Phe—L—(NO$_2$)Arg, Cbz—Gly—L—Phe—L—Phe, and Cbz—Gly—L—Phe—L—Phe—Gly (see Server and Wolinsky, supra, p. 523). These oligopeptides are inhibitors of Sendai virus activity. Cbz—Phe—D—Ala has also been tested against measles and herpes viruses (see Nicolaides, E. et al., supra).

It would be of great interest to extend the antiviral peptide findings of the prior art to other viral species, including mumps virus.

The fusion (F) protein of mumps virus is composed of two disulfide-linked gl

Ile—Ala—Ile—Gly—Ile—Ala—Ala—Leu—Gly—Val,

Ile—Ala—Ile—Gly—Ile—Ala—Ala—Leu—Gly—Val—Ala,

Ile—Ala—Ile—Gly—Ile—Ala—Ala—Leu—Gly—Val—Ala—Thr,

Ile—Ala—Ile—Gly—Ile—Ala—Ala—Leu—Gly—Val—Ala—Thr—Ala,

Ile—Ala—Ile—Gly—Ile—Ala—Ala—Leu—Gly—Val—Ala—Thr—Ala—Ala,

Ile—Ala—Ile—Gly—Ile—Ala—Ala—Leu—Gly—Val—Ala—Thr—Ala—Ala—Glu,

Ile—Ala—Ile—Gly—Ile—Ala—Ala—Leu—Gly—Val—Ala—Thr—Ala—Ala—Glu—Val, and

Ile—Ala—Ile—Gly—Ile—Ala—Ala—Leu—Gly—Val—Ala—Thr—Ala—Ala—Glu—Val—Thr.

The amino acid residue corresponding to the carboxyl terminus of any of the shown peptides can either be the true carboxyl terminus, or its salts, esters or amides, or it may be linked to a further amino acid residue or residues. In other words, the shown peptides may be part of longer oligo or polypeptides. The same is true of the amino end of the shown peptides. If either the shown N-terminus or the shown C-terminus, or both, are flanked by additional peptide sequences, then the overall polypeptide should, preferably, not be identical with the naturally occurring $F_1$ or $F_0$ mumps virus proteins.

Preferably the C-terminus residue has the formula $Y-CO-R^1$ wherein Y is as indicated above, $R^1$ is OM or $NR^2R^3$, where M is hydrogen, a pharmaceutically acceptable salt, or a $C_1-C_6$ branched or unbranched alkyl ester; and $R^2$ and $R^3$ are the same or different and selected from the group consisting of hydrogen, $C_1-C_6$ branched or unbranched alkyl, or both $R_2$ and $R_3$ taken together with the nitrogen atom form a five or six membered heterocyclic ring.

These peptides are useful as antiviral agents, by themselves or in combination, alone or in appropriate compositions. They are also useful as immunogens for the generation of antisera, for example in vaccination procedures in which case they may be mixed with or conjugated to appropriate carrier molecules or adjuvants. Another use for the peptides of the invention is as antigen analogues in labelled form for competitive immunoassay procedures in the detection of a virus such as mumps virus.

BRIEF DESCRIPTION OF THE PREFERRED EMBODIMENTS

The peptide sequences of the invention comprise a first amino acid residue (position 1) which is phenylalanine. This residue may be either in the D- or L-configuration, the D-configuration being preferred. The remaining amino acid residues are preferably in the L-configuration. The phenylalanine residue at position 1, furthermore, can be either in the free amine form (i.e. Z is hydrogen), or in acylated or protected amine form. $C_1-C_6$ acyl groups such as acetyl, trifluoroacetyl, propionyl, butyryl or benzoyl are useful. The amino group of the phenylalanine residue may, however, also be protected by an appropriate amino-protecting group. Among the preferred protecting groups are benzyloxycarbonyl (Cbz), t-butyloxycarbonyl, tosyl, trityl, phthalolyl, or trifluoroacetyl.

The carboxy terminus residue of the sequence, which may be any of several as indicated above, is either in free acid form (wherein $R^1$ is OH), or in ester, amide or pharmaceutically acceptable salt form. $C_1-C_6$ branched or unbranched alkyl esters are preferred and $C_1-C_6$ branched or unbranched alkyl amides, either primary or secondary, are also preferred. Alternatively, cyclic amides, such as piperidine and pyrrolidine can also be utilized. The esters or amides can also be utilized as intermediates or stable forms of the peptides of the invention. Readily known hydrolysis, either chemical or enzymatic, can then be utilized to generate the free acids or salts.

Among the preferred pharmaceutically acceptable salts are alkaline and alkaline-earth metal salts such as lithium, sodium, potassium, rubidium, cesium, calcium, magnesium, manganese, barium, or other metals such as zinc, copper, etc. Other pharmaceutically acceptable salts include amine cations derived from primary, secondary or tertiary amines. Examples of primary amines are methylamine, dimethylamine, trimethylamine, ethylamine, dibutylamine, triisopropylamine, N-methylhexylamine, decylamine, allylamine, cyclopentylamine, dicyclohexylamine, benzylamine, dibenzylamine, alpha-phenylethylamine, beta-phenylethylamine, ethylene diamine, diethylene triamine and the like. Aliphatic, cycloaliphatic and aryl-aliphatic amines containing up to and including about 18 carbon atoms as well as heterocyclic amines, such as piperidine, morpholine, pyrrolidine, piperazine, and lower alkyl derivatives thereof, such as 1-methylpiperidine, 4-ethylmorpholine, 1-isopropylpyrrolidine, 2-methylpyrrolidine, 1,4-dimethylpiperazine, as well as amines containing water solubilizing or hydrophilic groups such as mono-, di- and triethanlamine, epinephrine, procaine, and the like, can also be used.

Suitable pharmacologically acceptable quaternary ammonium cations are tetramethylammonium, tetraethylammonium, benzyltriethylammonium, phenyltriethylammonium, and the like.

The peptides can be by themselves or as part of acid addition salts of such acids as hydrohalic acids, carboxylic acids, and the like. Suitable hydrohalic acids include HCl, HBr, HF. Suitable carboxylic acids include acetic acid, trifluoroacetic acid, benzoic acid, and the like.

The peptides can be by themselves or be a part of longer sequences. In other words, the sequence corresponding to these peptides, when part of longer peptides, are still part of the present invention, and should be so construed, especially if performing the same functions as herein described.

Among the preferred peptides of the invention are Cbz—D—Phe—L—Ala—L—Gly; Cbz—D—Phe—L—Ala—L—Gly—L—Ile; and Cbz—D—Phe—L—Ala—L—Gly—L—Ile—L—Ala.

The peptides of the invention can be utilized as antiviral compounds. The antiviral activity is utilizable not only for mumps virus, but also for other kinds of viruses such as Sendai, SV-5, measles and the like. The latter viruses have substantial sequence homology in the N-terminus of their $F_1$ proteins with that of the mumps virus described in this invention.

Another use for the peptides of the present invention is as immunogens, either by themselves or preferably in association, either covalent or non-covalent, with appropriate carriers and/or adjuvants. Standard carriers such as bovine serum albumin, human serum albumin, keyhole limpet hemocyanin, tetanus toxoid, diptheria toxoid, thyroglobulin, ovalbumin, and purified protein derivative can be used and the peptides associated therewith. Upon inoculation into an appropriate host, under appropriate protocols, the host develops antibodies thereto. The antibodies can then be utilized in various processes such as passive immunization, immunoaffinity purification, immunoassay techniques, and the like. Lymphocytes derived from the host can be processed by known fusion techniques to produce appropriate hybridomas. The immunization using the peptides and/or carriers or adjuvants can also be used as a primary vaccination step, in which case, the peptides of the invention can form part of vaccine compositions.

Yet another use for the peptides of the invention is as antigen analogues in immunoassay procedures. A peptide of the invention can be labelled as, for example, by covalent linking to an enzyme (e.g., alkaline phosphatase, or horseradish peroxidase), a radiolabel (e.g., $C^{14}$ or $H^3$), or a fluorescent dye (fluorescein), and used in a competitive immunoassay mode. Competition between the labelled peptide of the invention and mumps virus (or any other virus having a close homology relationship to the peptide) for the active site of a given antibody and eventual determination of the label gives a quantitative measure of the amount of virus present within a given sample. Immunoassays techniques are well known to those of skill in the art.

The peptides can also be insolubilized by attachment thereof to appropriate insoluble solid phases such as latex particles or beads, and used in agglutination techniques for the determination of antiviral antibodies in a sample.

When used as antiviral agents, the peptides are formulated in appropriate carriers. They may be employed in dosage form such as tablets, capsules, powder packets or liquid solutions, suspensions or elixirs. Sterile liquid formulations such as solutions or suspensions can be prepared for parenteral use. In such compositions, the active ingredient will ordinarily always be present in an amount of 0.5% by weight based on the total weight of the composition and up to 99.9% by weight thereof.

Administration can be by any means that promptly ensures their antiviral effect. The compounds can be administered parenterally, subcutaneously, intravenously, intramuscularly, intraperitoneally, by transfusion or topically. The dosage administered will depend upon the age, health and weight of the recipient, kind of concurrent treatment if any, frequency of treatment, and the nature of the effect desired. Generally, daily oral dosage of the active ingredient compounds will be from about 50 mg to 150 mg per kg of body weight.

The peptides can be prepared by methods well known in the art of polypeptide synthesis (see, for example, Bodanszky, M., et al., "Peptide Synthesis (Second Edition)," G. A. Olah, ed. (John Wiley & Sons, New York, 1976) or Considine, "Chemical and Process Technology Encyclopedia," EPA 22-824. When synthesis is carried out in homogeneous phase, the peptide is obtained through the condensation of an amino acid or peptide containing a free carboxyl group and an amino acid or peptide containing a free amino group. A definite sequence can be constructed by repeating condensation with individual amino acid residues following the sequence by stepwise elongation or in some case, by the condensation between two preformed peptide fragments. In such condensations, the amino and carboxy groups which are not to participate in the reaction must be blocked. Blocking groups should be readily introduced, stable to the condensation reaction and removed selectively from the accomplished peptide.

Amino groups can be protected with a wide range of reagents. N-alkoxycarbonylation with benzyl or t-butyl chlorocarbonate is most widely used since the blocking group is readily decomposed by heating with HBr in glacial acetic acid. Other examples for amino blocking are propylation, tritylation, and phthaloylation or trifluoroacetylation. Carboxyl groups are protected usually through formation of the ester. Once the peptide bond is formed, the ester linkage is hydrolyzed selectively in dilute alkaline solution at room temperature. Hydroxyl groups should also be adequately blocked during peptide condensation reactions. The blocking must be stable to unmasking of the alpha-amino or alpha-carboxy group for stepwise condensation and must be readily removed at the final stage. Formation of the peptide bonds from amino and carboxyl components is accomplished by activation of the carboxyl components as acid halides, anhydrides, or esters. Peptide synthesis has been automated by use of solid phase supports (Merrifield) synthesis. Thus, both homogeneous and heterogeneous synthetic procedures can be used to prepare the peptides of the present invention.

The final products can be purified by various chromatographic procedures such as silica gel, alumina gel, gel permeation, ion exchange, high performance liquid chromatography, hydrophobic chromatography, and the like.

Another method of synthesis is by expression of a genetic sequence coding for any desired peptide of the invention. The genetic sequence may be present in an appropriate host such as a microorganism, i.e., a bacterium or yeast, or in a tissue culture host. Genetic sequences coding for any desired peptide can be constructed, integrated into an appropriate vehicle such as a plasmid or other vector, and transformed into the desired hosts.

Having now generally described the invention, the same will become better understood by reference to certain specific examples, which are included for purposes of explanation only and are not intended to be limiting unless otherwise specified.

I. DETERMINATION OF THE SEQUENCE OF THE AMINO TERMINUS OF THE MUMPS VIRUS F1 PROTEIN

A. MATERIALS AND METHODS

Figure 1:
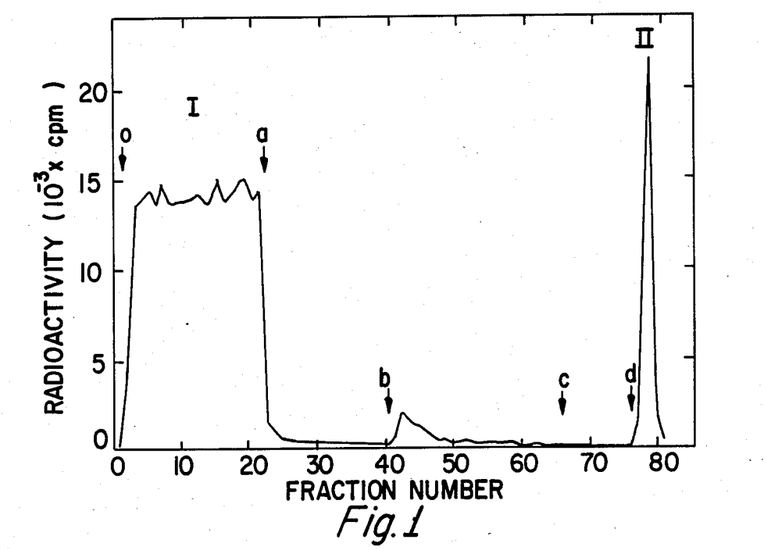
FIG. 1 shows the immunoaffinity purification of the mumps virus F protein.
Figure 2:
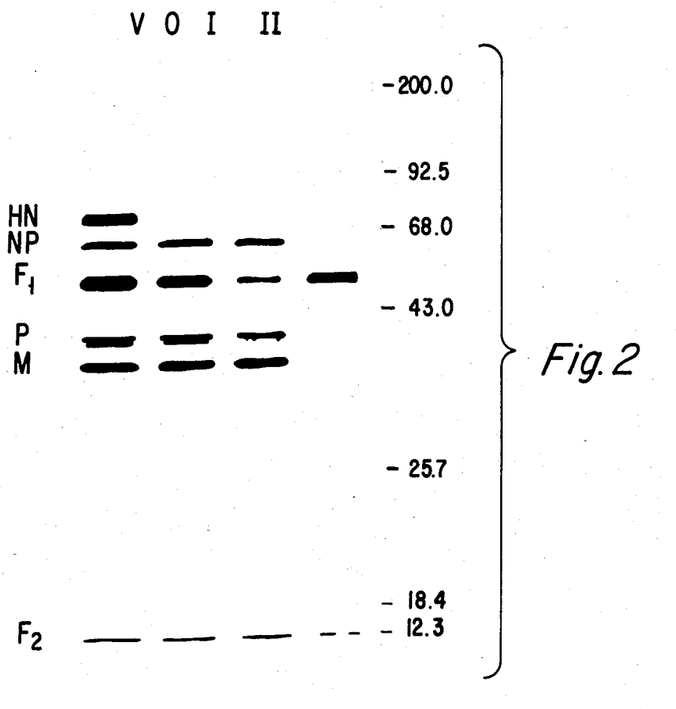
FIG. 2 shows a fluorogram for an SDS-PAGE under reducing conditions. The proteins of mumps virus are shown in lane V. The designations to the left of lane V used to label the polypeptide bands are as follows: HN: hemagglutinin neuraminidase; NP: nucleocapsid protein; $F_1$: $F_1$ polypeptide chain of the F protein; P: polymerase; M: membrane protein; $F_2$: $F_2$ polypeptide chain of the F protein. Electrophoretic mobilities of protein standards of known molecular weights are indicated to the right of lane II. Standards used were myosin H chain (200.0 kDA); phosphorylase B (92.5 kDA); bovine serum albumin (68.0 kDA); ovalbumin (43.0 kDA); alpha-chymotrypsinogen (25.7 kDA); betalactoglobin (18.4 kDA); and cytochrome C (12.3 kDA).

Virus: The Kilham strain of mumps virus (Kilham, L., *Journal of the American Medical Association* 146: 1231–1232 (1951)) was grown in CV-1 cells in the presence of [$^3$H]-leucine and was isolated as described in Server, et al. (*Infection and Immunity* 35: 179–186 (1982)).

Immunoaffinity Chromatography: Monoclonal antibodies against the glycoproteins of mumps virus were generated and characterized as described in Server, et al., supra. The antibodies were precipitated from mouse ascites fluids with ammonium sulfate and coupled to an activated affinity support, Affigel-10 (Bio-Rad), according to the procedure of Staehelin, et al., *Journal of Biological Chemistry* 256: 9750–9754 (1981). Immunoaffinity chromatography was performed using a modification of the method of Staehelin, et al., supra. Purified mumps virus was disrupted in 0.025M Tris HCl, pH 7.5 containing 0.15M NaCl, 0.1% SDS, 1.0% (w/v) sodium deoxycholate, 1.0% (w/v) Triton X-100, 0.002M phenylmethyl-sulfonyl fluoride and 100 Kallikrein Inhibitor Units/ml Aprotinin (Sigma) (Buffer A). The virus lysate was centrifuged at 95,000×g for one hour, and the supernatant was applied to the immunoaffinity column (3 ml bed volume) at a flow rate of 10 ml/hr. Following application of the virus lysate, the column was washed with Buffer A (13 bed volumes), Buffer B (0.025M Tris HCl, pH 7.5 containing 0.5M NaCl and 0.2% Triton X-100) (26 bed volumes) and Buffer C (0.15M NaCl with 0.1% Triton X-100) (10 bed volumes) at a flow rate of 30 ml/hr. Specifically bound virus glycoprotein was eluted from the column with 0.2N acetic acid, pH 2.5 containing 0.15M NaCl and 0.1% Triton X-100 (Buffer D) at a flow rate of 10 ml/hr and precipitated from Buffer D: one volume of protein solution was mixed with 4 volumes of methanol:acetone (1:1 v/v), heated at 37° C. for 2 min, and the protein precipitate pelleted by centrifugation at 10,000×g for 30 min.

Alkylation and Reduction: The mumps fusion protein was reduced with 4.7 mM dithiotreitol in 7M guanidine-HCl/0.5M Tris-HCl, pH 8.2 containing 0.005M EDTA at 37° C. for 90 minutes. Excess iodoacetic acid was added, and the reaction was incubated for 1 hr at 37° C. and stopped by addition of glacial acetic acid.

High Performance Size Exclusion Chromatography: The mixture of the reduced and alkylated chains was lyophilized and redissolved in 7.5% trifluoroacetic acid/92.5% (v/v) elution buffer. The chains were separated on a Spherogel TSK-SW 3000 analytical column (Beckman) (0.75×30 cm) with an SW precolumn (Beckman) (0.75×10 cm) using a buffer of glacial acetic acid/propan-2-ol/water (20/15/65, v/v/v) (Brown, et al., *Analytical Biochemistry* 112: 128–134 (1981)) at a flow rate of 0.5 ml/min with detection at 280 nm.

Amino Acid Analysis: Amino acid compositions were determined using a Beckman 6300 analyser with Hewlett-Packard 3390A integrators after acid hydrolysis for samples in sealed, evacuated tubes (Pyrex, 6×50 mm) at 100° C. for 24 hr in constant boiling HCl (0.025 ml) (Pierce, Sequanal grade) (Moore, S., *Chemistry and Biology of Peptides,* Meienhofer, J., ed. (Ann Arbor Science, Ann Arbor, MI, 1972), pp. 629–653). Ninhydrin and two channel (440 and 570 nm) integration provided analysis of all amino acids, except tryptophan, cysteine, asparagine, glutamine, with 1–7% confidence values at 100 pmol/amino acid and with lower limit of detection of 25 pmol.

Protein Sequence Analysis: Protein sequence analysis of the mumps fusion protein ($F_{1-2}$) and the isolated $F_1$ and $F_2$ chains were determined with Applied Biosystems 470A protein sequencer. The sequence program (Hewick, R. M., et al., *Journal of Biological Chemistry* 256: 7990–7997 (1981)) contains one coupling step (44° C., 26 min), a single cleavage (44° C., 6.7 min), and automated conversion of the 2-anilino-5-thiazolinone derivatives (Pth-amino acids) using 25% trifluoroacetic acid (50° C., 33 min). Polybrene (Tarr, G. E., et al., *Analytical Biochemistry* 84: 622–627; Klapper, D. G., et al., *Analytical Biochemistry* 85: 126–131 (1978)) was added to the glass filter disc, and five sequence cycles were run to reduce Polybrene-related contaminants. The Pth-amino acids were identified by high performance liquid chromatography on IBM cyano columns, using a 15 mM sodium acetate buffer (pH 5.8) and a complex gradient of acetonitrile/methanol (92.5:7.5, v/v) (Hunkapiller, M. W. and Hood, L. E., *Methods of Enzymology* 91: 486–493).

SDS Polyacrylamide Gel Electrophoresis (SDS-PAGE): SDS-PAGE was performed under reducing conditions, according to the procedure of Laemmli, U.K. *Nature* (London) 227: 680–685 (1970). After electrophoresis, the gels were processed for fluorography by the method of Bonner, W. M. and Laskey, R. A., *European Journal of Biochemistry* 46: 83–88 (1974). Prestained protein standards (Bio-Rad) were used for molecular weight determinations.

B. RESULTS

Immunoaffinity Purification of Mumps Virus F Protein: Radiolabelled mumps virus was disrupted with detergent in Buffer A and used for the serial extraction of the virus glycoproteins (FIG. 1). The HN glycoprotein was removed quantitatively by immunoaffinity chromatography using an anti-HN monoclonal antibody (FIG. 2, lanes V,O). The effluent from the first column with the remaining mumps virus proteins was applied to a second immunoaffinity column containing an anti-F monoclonal antibody (FIGS. 1, 2). As shown in FIG. 2, removal of the F protein from the virus protein mixture was incomplete (lanes O, I), although residual F protein could be removed by reapplication of the effluent to the column. The F protein, eluted from the column at acid pH (FIG. 1, peak II), contained no detectable contamination by other radiolabeled virus proteins (FIG. 2, lane II). Moreover, amino acid analysis of the eluent from the column prior to the application of virus proteins indicated that no appreciable antibody was lost from the immunoaffinity matrix during acid elution. The purified F protein was precipitated from the detergent-containing eluent with methanol/acetone prior to reduction and alkylation or sequence analysis.

Figure 3:
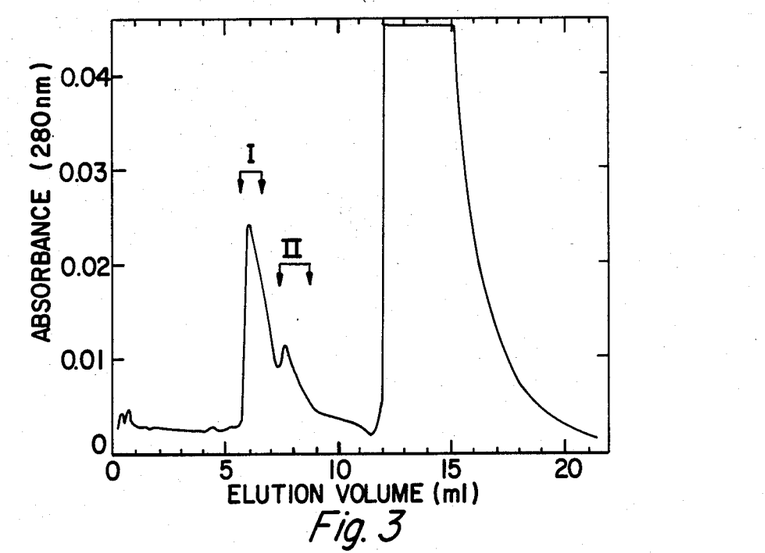
FIG. 3 shows the isolation of the $F_1$ and $F_2$ polypeptide chains of the F protein of mumps virus by high performance size exclusion chromatography.
Figure 4:
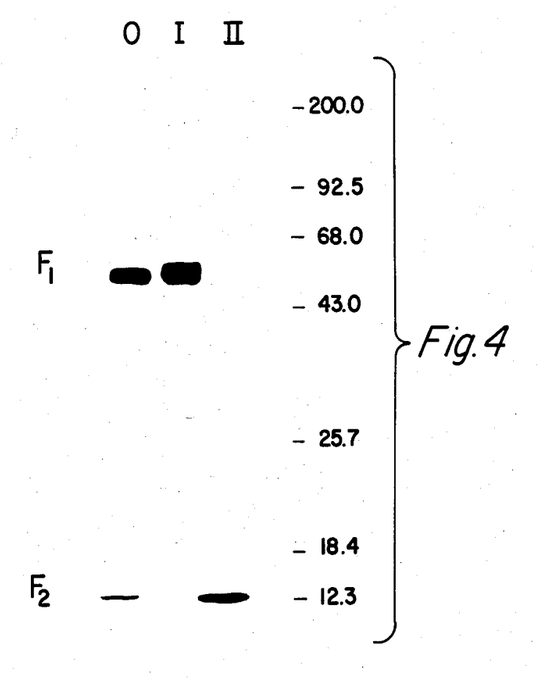
FIG. 4 shows a fluorogram for an SDS-PAGE performed under reducing conditions for the fractions of FIG. 3. Lane 0 shows the F protein of mumps virus prior to the separation of the $F_1$ and $F_2$ polypeptide chains. Aliquots from pools I and II are shown in lanes I and II, respectively. The electrophoretic mobilities of protein standards of known molecular weight (See FIG. 2) are indicated to the right of lane II.

Purification of the $F_1$ and $F_2$ Chains: Purified F protein was reduced and alkylated under denaturing conditions. The sample was applied to a high performance size exclusion chromatography column equilibrated with acetic acid/propan-2-ol/water (20/15/65, v/v/v). Three peaks were detected by UV absorbance at 280 nm (FIG. 3). The broad peak eluting in the inclusion volume (12–19 ml) was shown to contain guanidine-HCl by an analysis of the reduction and alkylation buffer in the absence of protein. Fractions from the other two peaks were pooled, and an aliquot from each pool was analyzed by SDS-PAGE. As illustrated in FIG. 4, the $F_1$ and $F_2$ chains were separated from one another: pool I contained $F_1$ (lane I) and pool II contained $F_2$ (lane II).

Protein Sequence Analysis of the $F_1$ and $F_2$ chains: The purified $F_1$ and $F_2$ peptide chains were sequenced by automated Edman degradation with a gas phase sequenator (Table I):

TABLE I

Sequence Data for the $F_1$ and $F_2$ Peptide Chains and for the F Protein[a]

| Cycle | $F_1$ | | $F_2$ | | F protein | | | Cycle |
|---|---|---|---|---|---|---|---|---|
| 1 | Phe | 81 | Val | 797 | Phe | 180 | Val | 307 | 1 |
| 2 | Ala | 55 | Asn | 675 | Ala | 230 | Asn | 255 | 2 |
| 3 | Gly | 71 | Ile | 270 | Gly | 190 | Ile | 257 | 3 |
| 4 | Ile | 64 | Asn | 574 | Ile | 226 | Asn | 191 | 4 |
| 5 | Ala | 55 | Ile | 301 | Ala | 193 | Ile | 301 | 5 |
| 6 | Ile | 80 | Leu | 274 | Ile | 272 | Leu | 195 | 6 |
| 7 | Gly | 35 | Gln | 321 | Gly | 164 | Gln | 142 | 7 |
| 8 | Ile | 48 | Gln | 380 | Ile | 193 | Gln | 208 | 8 |
| 9 | Ala | 51 | Ile | 428 | Ala | 168 | Ile | 212 | 9 |
| 10 | Ala | 60 | Gly | 377 | Ala | 190 | Gly | 196 | 10 |
| 11 | Leu | 36 | Tyr | 395 | Leu | 163 | Tyr | 171 | 11 |
| 12 | Gly | 134 | Ile | 203 | Gly | 140 | Ile | 57 | 12 |
| 13 | Val | 86 | Lys | 75 | Val | 138 | Lys | 53 | 13 |
| 14 | Ala | 31 | Gln | 117 | Ala | 129 | Gln | 67 | 14 |
| 15 | Thr | 15 | Gln | 183 | Thr | 54 | Gln | 107 | 15 |
| 16 | Ala | 22 | Val | 187 | Ala | 96 | Val | 56 | 16 |
| 17 | Ala | 15 | Arg | 277 | Ala | 118 | Arg | 63 | 17 |
| 18 | Gln | 16 | Gln | 74 | | Gln | 109 | | 18 |
| 19 | Val | 28 | Leu | 128 | Val | 92 | Leu | 78 | 19 |
| 20 | Thr | 13 | Ser | 91 | Thr | 35 | Ser | 18 | 20 |
| 21 | Ala | 13 | Tyr | 91 | Ala | 71 | Tyr | 78 | 21 |
| 22 | Ala | 23 | Tyr | 134 | Ala | 91 | Tyr | 107 | 22 |
| 23 | Val | 9 | Ser | 25 | Val | 60 | Ser | 9 | 23 |
| AL[b] | 213 | | 858 | | 454 | | | | |
| RY[c] | 95.3% | | 94.3% | | 95.3% | | 93.2% | | |

[a] Yields in picomoles of 3-phenyl-2-thiohydantoin(Pth)-amino acids plus phenylthiocarbamyl(Ptc)-amino acids, when present, minus background of corresponding amino acids.
[b] AL - amounts loaded based on amino acid analyses (this application) and molecular weight estimates (Herrler and Compans, Virology 47: 354-362 (1983).
[c] RY - repetitive yields calculated from yields of representative, stable, Pth-amino acids.

Twenty three amino acid residues were identified for each chain in the following sequences:

$F_1$ NH$_2$—Phe—Ala—Gly—Ile—Ala—Ile—Gly—Ile—Ala—
    1                              5

—Ala—Leu—Gly—Val—Ala—Thr—Ala—Ala—Gln—Val—
    10                              15

—Thr—Ala—Ala—Val—
    20

$F_2$ NH$_2$—Val—Asn—Ile—Asn—Ile—Leu—Gln—Gln—Ile—
    1                              5

—Gly—Tyr—Ile—Lys—Gln—Gln—Val—Arg—Gln—Leu—
    10                              15

—Ser—Tyr—Tyr—Ser—
    20

An analysis of the intact F protein revealed a mixture sequence with two residues per degradative cycle, corresponding to the residues of the $F_1$ and $F_2$ chains (Table I).

II. SYNTHESIS OF PEPTIDES CORRESPONDING TO THE AMINO TERMINUS OF THE MUMPS VIRUS F1 PROTEIN

Peptides of five and fourteen amino acids corresponding to the amino terminal sequence of the mumps virus F1 protein were synthesized with either a L-Phe or D-Phe at the amino terminus. Using standard solid phase methods (Barany, G. and Merrifield, R. B. (1980) In: "The Peptides" (Gross, E. and Meienhofer, J., Eds.) Vol. 2, Academic, New York; Rosenblatt, M., Goltzman, d., Keutmann, H. T., Tregear, G. W., and Potts, J. T., Jr. (1976) J. Biol. Chem. 251:159–164), the peptides were synthesized on solid supports of hydroxymethyl resin (Penisula derivatized initially with Boc—Ala (0.15 to 0.4 meq alanine/g by coupling in the presence of dicyclohexylcarbodiimide and dimethylaminopyridine in dimethylformamide (DMF). Deprotection of the amino terminal t-butyloxycarbonyl (Boc) protecting group was with 40% trifluoroacetic acid in dichloromethane (10 ml/g) for 30 min at ambient temperature. After washing with dichloromethane (3×10 ml/g resin), the neutralization was with 25% diisoporpylethylamine in dichloromethane (10 ml/g resin). After additional washing with dichloromethane (3×10 ml/g resin), the subsequent Boc-amino acid (3 molar excess) was coupled in DMF (10 ml/g resin) using dicylclohexylcarbodiimide (3.3. molar excess) for 2 hours at room temperature. The resin was washed first with DMF and then with dichloromethane (3×10 ml/g resin) to remove the unreacted Boc-amino acid. The procedure was repeated for the addition of the next Boc-amino acid. After the N-terminal most amino acid was added, and the Boc protecting group was removed, the resin was washed with ethanol and dried in vacuo. The peptide was cleaved from the resin by HF (10 ml/g resin) with anisole (1 ml/g resin) at 0° C. for 60 minutes (Sakakibara, S. (1971) in "Chemistry and Biology of Amino Acids, Peptides, and Proteins" (B. Weinstein, ed.), Vol. 1, pp. 51–85, Dekker, N.Y.). After drying the resin in vacuo, the residual anisole was extracted by diethyl ether, and the peptide was extracted from the resin by glacial acetic acid. The peptides were recovered by lyophilization of the glacial acetic acid diluted with distilled water (1:10, v/v). The N-terminus of the pentapeptides was blocked with benzyloxycarbonyl (Cbz) Bergmann, M. and Zervas, L. (1932) Ber. Dtsch. Chem. Gr. 65:1192–1201). Peptides were characterized by amino acid analysis and analytical reverse phase high performance chromatography. The sequence of selected peptides was confirmed by protein sequence analysis (Hewick, R. M., Hunkapiller, M. W., Hood, L. E., and Dryer, W. J. (1981) J. Biol. Chem. 256:7990–7997).

DISCUSSION

Figure 5:
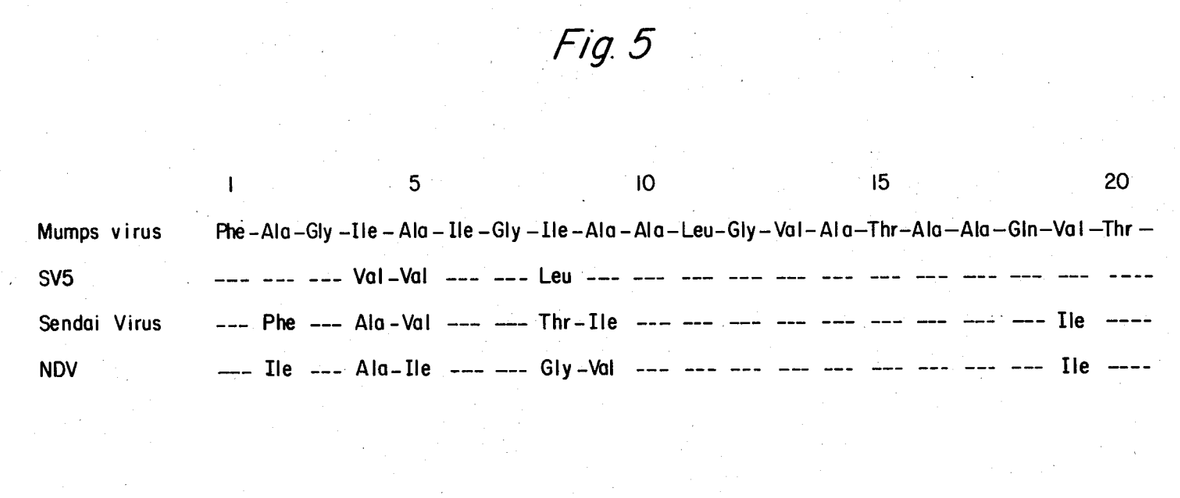
FIG. 5 shows a comparison of the N-terminal sequence of the $F_1$ polypeptide of the mumps virus with those of three other paramyxoviruses. The dashed lines indicate identity with the mumps virus sequence. Sequence data for SV5, Sendai virus and NDV are from Richardson, et al., (supra, 1980).

Sub-nanomole quantities of the F protein of mumps virus were obtained by immunoaffinity chromatography using an anti-F monoclonal antibody. The high degree of specificity afforded by the use of a monoclonal antibody allowed the isolation of purified F protein with no detectable contamination. This material was subjected to amino acid sequence analysis both before and after reduction and alkylation, and twenty-three amino acids from the N-terminus of each of the peptide chains of the F protein were identified. The N-terminus of the $F_1$ chain of mumps virus shows a high degree of sequence homology with the corresponding regions of the F proteins of SV-5, Sendai virus, and NDV (FIG. 5). Fourteen of the first twenty amino acid residues at the N-terminus of the $F_1$ chains are conserved among the four viruses; amino acid substitutions, when they occur, are invariably at positions 2, 4, 5, 8, 9, and 19 in the sequence.

Having now fully described the invention it will be appreciated that the same can be performed within a broad and equivalent range of parameters, structures and conditions without affecting the spirit or scope thereof of or any embodiment thereof.

What is claimed as new and intended to be covered by Letters Patents of the United States is:

1. A peptide comprising the following sequence:

X—NH—Ala—Gly—Y wherein X is D— or

L-Z—NH—CH—CO—
            |
            CH$_2$
            |
            C$_6$H$_5$ where Z is hydrogen, $C_1$–$C_6$ acyl, aroyl or an amino-protecting group; and
   Y is selected from the group consisting of
   Ile,
   Ile—Ala,
   Ile—Ala—Ile,
   Ile—Ala—Ile—Gly,
   Ile—Ala—Ile—Gly—Ile,
   Ile—Ala—Ile—Gly—Ile—Ala,
   Ile—Ala—Ile—Gly—Ile—Ala—Ala,
   Ile—Ala—Ile—Gly—Ile—Ala—Ala—Leu,
   Ile—Ala—Ile—Gly—Ile—Ala—Ala—Leu—Gly,
   Ile—Ala—Ile—Gly—Ile—Ala—Ala—Leu—Gly—Val,
   Ile—Ala—Ile—Gly—Ile—Ala—Ala—Leu—Gly—Val—Ala,
   Ile—Ala—Ile—Gly—Ile—Ala—Ala—Leu—Gly—Val—Ala—Thr,
   Ile—Ala—Ile—Gly—Ile—Ala—Ala—Leu—Gly—Val—Ala—Thr—Ala,
   Ile—Ala—Ile—Gly—Ile—Ala—Ala—Leu—Gly—Val—Ala—Thr—Ala—Ala,
   Ile—Ala—Ile—Gly—Ile—Ala—Ala—Leu—Gly—Val—Ala—Thr—Ala—Ala—Glu,
   Ile—Ala—Ile—Gly—Ile—Ala—Ala—Leu—Gly—Val—Ala—Thr—Ala—Ala—Glu—Val,
   and
   Ile—Ala—Ile—Gly—Ile—Ala—Ala—Leu—Gly—Val—Ala—Thr—Ala—Ala—Glu—Val—Thr.

2. The peptide of claim 1 wherein X is

Z—D—NH—CH—CO—.
          |
          CH$_2$
          |
          C$_6$H$_5$ 3. The peptide of claim 1 wherein X is Cbz—D-NH—CH—CO—.
           |
           CH$_2$
           |
           C$_6$H$_5$ 4. The peptide of any of claims 1, 2 or 3 wherein Y is Ile.

5. The peptide of any of claims 1, 2 or 3 wherein Y is Ile—Ala.

6. The peptide of any of claims 1, 2 or 3 wherein Y is Ile—Ala—Ile.

7. The peptide of any of claims 1, 2 or 3 wherein Y is Ile—Ala—Ile—Gly.

8. The peptide of claim 1 wherein the C—terminus thereof has the formula

Y—CO—R$^1$ wherein Y is as indicated;
   $R_1$ is OM or NR$^2$R$^3$;
   where M is hydrogen, a pharmaceutically acceptable salt, or a $C_1$–$C_6$ branched or unbranched alkyl group; and
   R$^2$ and R$^3$ are the same or different and selected from the group consisting of hydrogen, $C_1$–$C_6$ branched or unbranched alkyl, or both $R_2$ and $R_3$ taken together with the nitrogen atom form a five or six membered heterocyclic ring.

9. The peptide of claim 8 wherein R$^1$ is OM.

10. The peptide of claim 9 wherein M is H or a pharmaceutically acceptable salt.

11. A compound of the formula

Cbz—D-HN—CH—CO—NH—Ala—Gly—Ile—Ala—COOM
                |
                CH$_2$
                |
                C$_6$H$_5$ where M is hydrogen or a pharmaceutically acceptable salt.

12. A compound of the formula where M is hydrogen or a phramceutically acceptable salt.

13. A composition useful for antiviral treatment comprising an effective amount of a peptide according to claim 1 together with a phramacologically inert carrier.

* * * * *